(12) United States Patent
Nakabayashi (10) Patent No.: US 8,971,987 B2
(45) Date of Patent: Mar. 3, 2015

(54) SUBJECT INFORMATION ACQUIRING APPARATUS

(71) Applicant: Canon Kabushiki Kaisha, Tokyo (JP)

(72) Inventor: Takaaki Nakabayashi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 182 days.

(21) Appl. No.: 13/776,200

(22) Filed: Feb. 25, 2013

(65) Prior Publication Data
US 2013/0225970 A1    Aug. 29, 2013

(30) Foreign Application Priority Data

Feb. 29, 2012   (JP) ................................ 2012-043808

(51) Int. Cl.
*A61B 5/05* (2006.01)
*A61B 8/00* (2006.01)
*A61B 5/00* (2006.01)
*A61B 8/08* (2006.01)

(52) U.S. Cl.
CPC ............. *A61B 8/4444* (2013.01); *A61B 5/0095* (2013.01); *A61B 5/708* (2013.01); *A61B 5/704* (2013.01); *A61B 8/406* (2013.01); *A61B 8/0825* (2013.01); *A61B 5/4312* (2013.01); *A61B 8/4209* (2013.01); *A61B 8/4281* (2013.01); *A61B 2562/14* (2013.01)
USPC ........................................................ 600/407

(58) Field of Classification Search
CPC .... A61B 8/4444; A61B 5/0095; A61B 5/708; A61B 5/704; A61B 8/406; A61B 8/0825; A61B 5/4312; A61B 8/4209; A61B 8/4281; A61B 2562/14
USPC ........................................................ 600/407
See application file for complete search history.

(56) References Cited

FOREIGN PATENT DOCUMENTS

| JP | 2011-103913 A | 6/2011 | | |
|---|---|---|---|---|
| WO | WO 2005122904 A1 | * | 12/2005 | ............... A61B 8/00 |
| WO | WO 2011058724 A1 | * | 5/2011 | ............... A61B 8/08 |

* cited by examiner

*Primary Examiner* — Long V Le
*Assistant Examiner* — Katherine McDonald
(74) *Attorney, Agent, or Firm* — Canon USA Inc. IP Division (57) ABSTRACT

A subject information acquiring apparatus includes a subject-holding member which holds a subject and a probe unit having a transducer which receives acoustic waves from the subject through the subject-holding member, a housing which accommodates the transducer, and a matching liquid-holding member configured to hold a matching liquid between the transducer and the subject-holding member, the probe unit being allowed to move relative to the subject-holding member. The probe unit has a guide which introduces the matching liquid to the subject-holding member, the matching liquid having been spilled from a space defined by the matching liquid-holding member, the transducer, and the subject-holding member onto the upper surface of the hosing and then flowed from the upper surface of the housing.

6 Claims, 7 Drawing Sheets

SUBJECT INFORMATION ACQUIRING APPARATUS

BACKGROUND OF THE INVENTION

1. Field of the Invention

The present invention relates to a subject information acquiring apparatus which receives acoustic waves from a subject.

2. Description of the Related Art

Japanese Patent Laid-Open No. 2011-103913 discloses a subject information acquiring apparatus which utilizes a photoacoustic effect, in which acoustic waves from a subject irradiated with light are received with a probe to create an image representing information on the subject. In this apparatus, a breast being the subject is held with two subject-holding members facing each other, and the probe is two-dimensionally moved in horizontal and vertical directions along the subject-holding members to receive acoustic waves. A housing which accommodates the probe (transducer) has an oil sealing portion which enables a matching liquid such as oil to be held between the probe and the subject-holding member for acoustic impedance matching. The upper surface of the oil sealing portion has an opening to remove bubbles contained in the matching liquid. The matching liquid which has spilled or overflowed from the opening runs down the subject-holding member and is then retrieved to a tank by a retrieving mechanism.

The apparatus disclosed in Japanese Patent Laid-Open No. 2011-103913 gives no consideration to the case in which matching liquid flows out of the opening onto the upper surface of the housing (namely, the matching liquid on the upper surface of the housing). Part of the matching liquid on the upper surface of the housing runs down a side surface of the housing and the back surface thereof (opposite side of the subject-holding member relative to the probe). In particular, in the apparatus disclosed in Japanese Patent Laid-Open No. 2011-103913, the matching liquid which has spilled from the opening onto the upper surface of the housing directly falls down from the lower part of the housing without running down the subject-holding member. In the case where the fallen matching liquid does not land on a tray provided below the subject-holding member, the matching liquid cannot be retrieved, leading to possible fear of a decrease in the total amount of the matching liquid. Even in the case where the matching liquid which has not run down the subject-holding member falls on the tray, the matching liquid splashes, which leads to a decrease in the total amount of the matching liquid and makes the interior of the apparatus dirty in some cases.

SUMMARY OF THE INVENTION

The present invention provides a subject information acquiring apparatus which enables a matching liquid flowing from the upper surface of a housing to run down a subject-holding member.

An aspect of the present invention provides a subject information acquiring apparatus including a subject-holding member which holds a subject and a probe unit having a transducer which receives acoustic waves from the subject through the subject-holding member, a housing which accommodates the transducer, and a matching liquid-holding member configured to hold a matching liquid between the transducer and the subject-holding member, the probe unit being allowed to move relative to the subject-holding member, wherein the probe unit has a guide which introduces the matching liquid toward the subject-holding member, the matching liquid having been spilled from a space defined by the matching liquid-holding member, the transducer, and the subject-holding member onto the upper surface of the hosing and then flowed from the upper surface of the housing.

Such an aspect of the present invention enables the matching liquid flowing from the upper surface of the housing to run down the subject-holding member, which can prevent a reduction in the amount of the matching liquid and contribute to keeping the interior of the apparatus clean.

Further features of the present invention will become apparent from the following description of exemplary embodiments with reference to the attached drawings.

DESCRIPTION OF THE EMBODIMENTS

In the present invention, a probe unit has a guide configured to introduce a matching liquid from a housing to a subject-holding member, so that the matching oil flowing down from the upper surface of the housing is guided to the subject-holding member.

In the present invention, acoustic waves include elastic waves such as a sound wave, an ultrasonic wave, a photoacoustic wave, and an optical ultrasonic wave, and the probe receives the acoustic waves propagated inside a subject. The subject information acquiring apparatus of the present invention includes an apparatus in which a subject is irradiated with light beams (electromagnetic waves including visible light beams and infrared rays) to generate acoustic waves inside the subject and the acoustic waves are received to acquire information on the subject.

Information on a subject to be acquired indicates characteristic information reflecting a distribution of the initial sound pressure of acoustic waves generated by irradiation with light, a density distribution of light energy absorption derived from a distribution of the initial sound pressure, a distribution of an absorption coefficient, and concentration distributions of substances constituting tissues. The concentration distributions of substances are, for example, a distribution of oxygen saturation and a concentration distribution of oxygenated or reduced hemoglobin. The information on a subject may be acquired not only as numerical data but as a distribution of information in different sites of the subject. In particular, a distribution of information, such as a distribution of an absorption coefficient or a distribution of oxygen saturation, may be acquired in the form of image data.

The subject information acquiring apparatus of the present invention may be an apparatus utilizing an ultrasonic pulse-echo technique, in which ultrasonic waves are transmitted to a subject and waves reflected inside the subject are received to acquire information on the subject. In the apparatus utilizing an ultrasonic pulse-echo technique, information on a subject to be acquired is characteristic information reflecting a difference in acoustic impedance between internal tissues of the subject.

Embodiments of the present invention will now be described with reference to the accompanying drawings. The same components are basically denoted by the same reference symbols to omit the repeated description thereof.

First Embodiment

Figure 1:
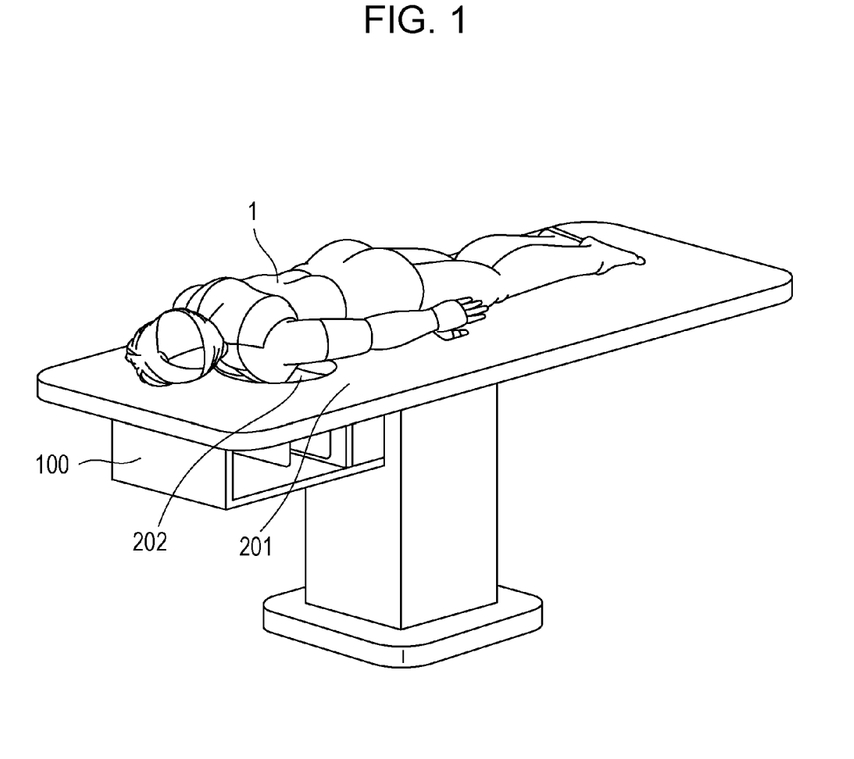
FIG. 1 is a schematic perspective view illustrating a subject information acquiring apparatus according to an embodiment of the present invention.

The present embodiment herein discussed gives an example of an apparatus in which a subject is irradiated with light beams and acoustic waves generated in the subject are received with a probe to acquire information on the subject. FIG. 1 is a schematic perspective view illustrating a subject information acquiring apparatus of the present embodiment. The subject information acquiring apparatus includes a supporting member 201 as a bed for supporting a test subject 1 and an examination unit 100 provided under the supporting member 201. The supporting member 201 has an opening 202 into which a subject such as a breast being body part of the test subject 1 is inserted. The examination unit 100 provided under the supporting member 201 receives acoustic waves from a subject.

Examination Unit

Figure 2:
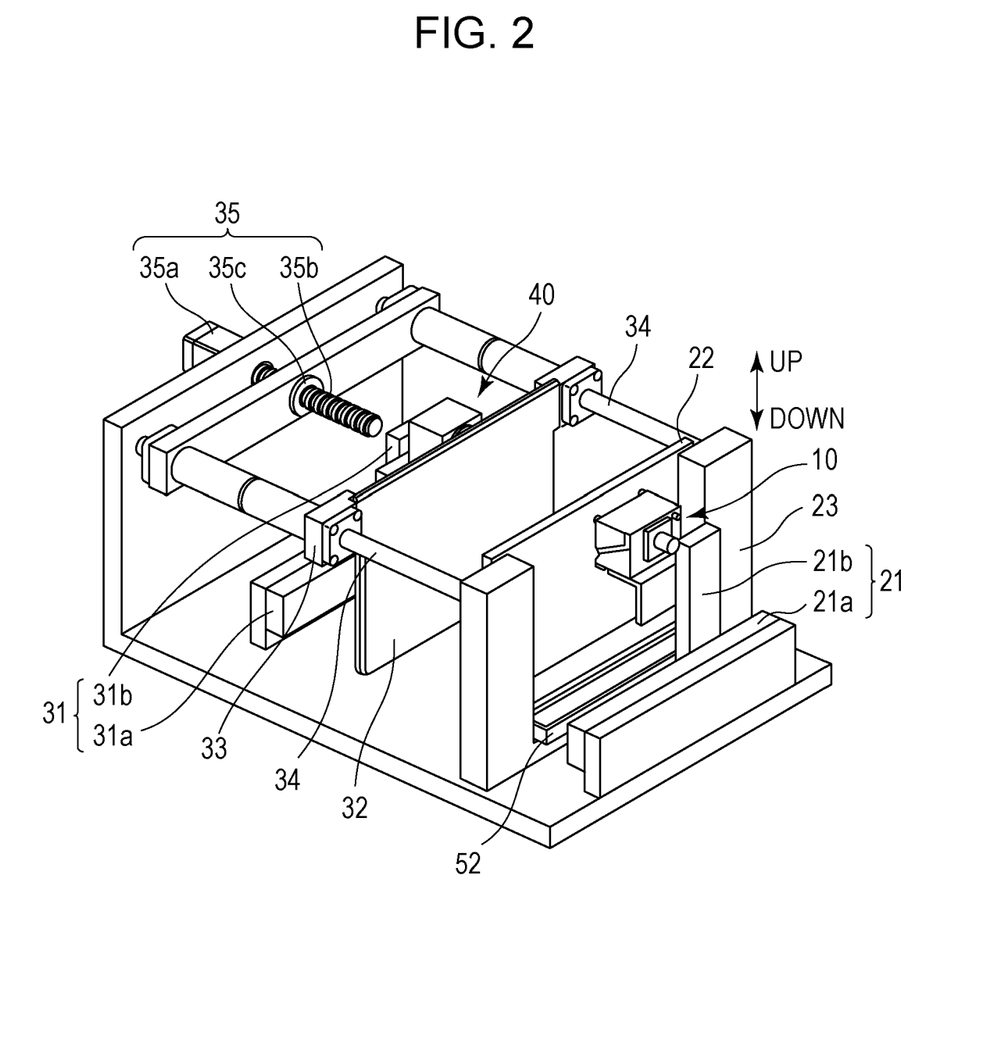
FIG. 2 is a schematic perspective view illustrating an examination unit according to an aspect of the present invention.

FIG. 2 is a perspective view illustrating the internal configuration of the examination unit 100. The examination unit 100 has a probe unit 10, an optical unit 40, and a fixing member 22 and movable holding member 32 being a subject-holding member. An oil tray 52 is provided below the fixing member 22 to retrieve matching oil spilled from a space (space 15 in FIG. 3B) formed between a probe inside the probe unit 10 and the fixing member 22. The oil tray 52 is disposed so as to catch matching oil running down the fixing member 22.

The probe unit 10 is attached to a probe-moving mechanism 21 having two shafts of a horizontal shaft 21a and a vertical shaft 21b and can therefore two-dimensionally move along the fixing member 22. The probe-moving mechanism 21 is controlled by a micro controller or computer (not illustrated) being a control unit. In the present embodiment, the supporting member 201 is provided as a counter member so as to overlie the probe unit 10. In the present invention, however, the counter member is not limited to the supporting member 201 and includes a member provided so as to overlie a region in which a probe can move, such as a reinforcing member for enhancing the strength of the subject-holding member. A direction in which gravity works (direction of gravity field) herein indicates "being downward (lower side)", and the direction opposite thereto herein indicates "being upward (upper side)".

Subject-Holding Member

A subject to be examined (not illustrated) is held so as to be pressed from two sides by the fixing member 22 and the movable holding member 32 provided relative to the fixing member 22. The fixing member 22 is preferably formed from a resin in view of acoustic impedance matching between a subject and the probe inside the probe unit 10, and an especially preferred material is polymethylpentene. The fixing member 22 is attached to a fixing plate 23, and the movable holding member 32 is attached to movable plates 33. The movable plates 33 are provided so as to be movable along guide rods 34 in a direction in which a subject is pressed to be held and are driven by a holding member-driving mechanism 35. The holding member-driving mechanism 35 includes a motor 35a, a ball screw 35b, and a nut 35c. Since component onto which the nut 35c is provided is connected to the movable plates 33, driving of the motor 35a enables the movable holding member 32 to move.

Optical Unit

The optical unit 40 is disposed so as to face the probe unit 10 with the fixing member 22 interposed therebetween. Light is introduced from a light source (not illustrated) to the optical unit 40 via an optical system, such as a fiber or a lens, and the light is emitted from a light emission end of an optical system inside the optical unit 40 to a subject through the movable holding member 32. A laser which generates pulsed light on the order of nanoseconds is used as the light source. The optical unit 40 can be two-dimensionally moved by an optical unit-moving mechanism 31 having two shafts of a horizontal shaft 31a and a vertical shaft 31b as in the probe driving unit 21. The optical unit-moving mechanism 31 is controlled by a micro controller or a computer (not illustrated) as in the probe-moving mechanism 21. The probe-moving mechanism 21 and the optical unit-moving mechanism 31 are controlled in synchronism, so that the optical unit 40 and probe unit 10 symmetrically disposed with a subject interposed therebetween can be always moved while being kept at symmetrical positions.

In the present embodiment, the probe unit 10 is disposed on the side of the fixing member 22, and the optical unit 40 is disposed on the side of the movable holding member 32; however, the present invention should not be limited to such a configuration. The probe unit 10 may be provided on the side of the movable holding member 32 or may be provided on the both sides of the fixing member 22 and the movable holding member 32. The optical unit 40 may be provided on the side of the fixing member 22 or may be provided on the both sides of the fixing member 22 and the movable holding member 32. Furthermore, a fiber or another component may be inserted into the probe unit 10 to emit light from the interior of the probe unit 10. The configuration of the probe unit 10 will now be described in detail.

Probe Unit

Figure 3A:
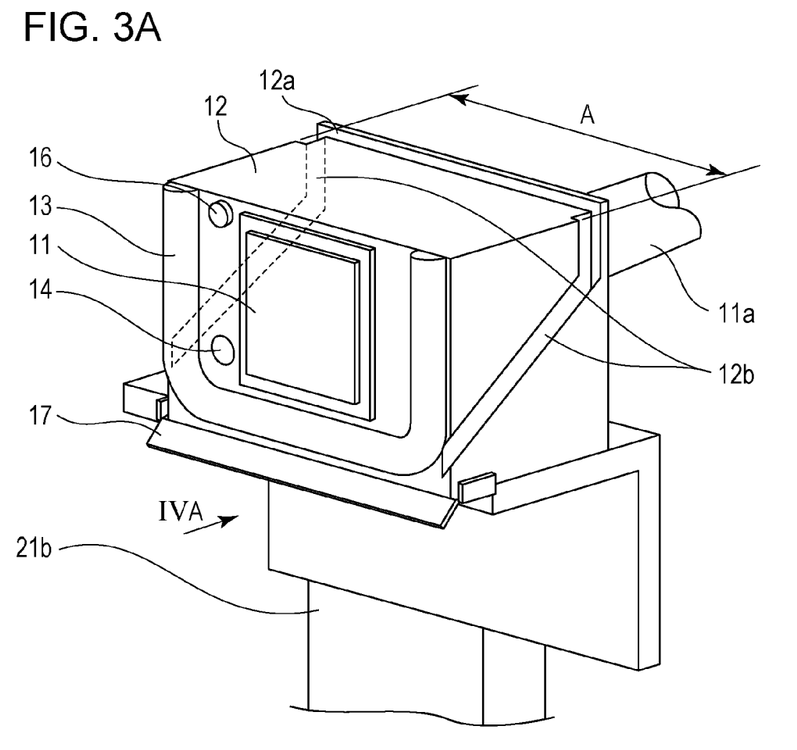
FIG. 3A is a schematic perspective view illustrating a probe unit according to a first embodiment of the present invention.
Figure 3B:
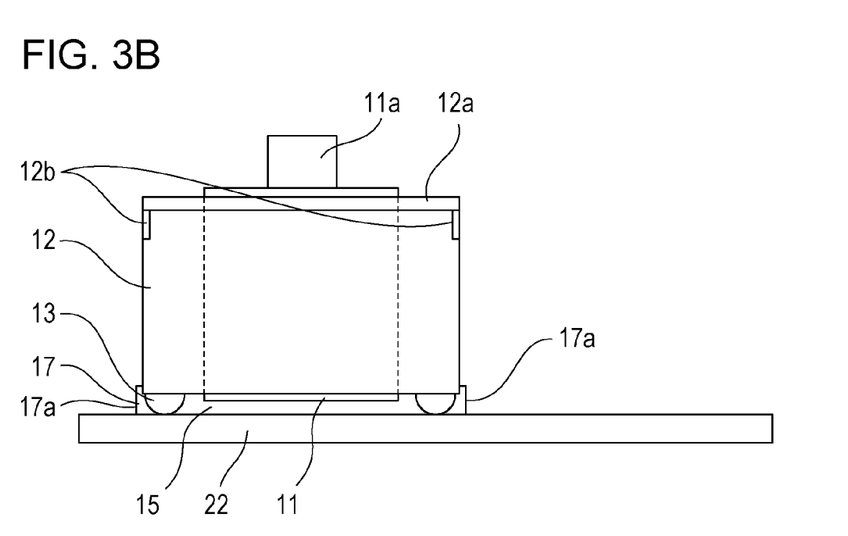
FIG. 3B is a schematic top view illustrating the probe unit according to the first embodiment of the present invention.

FIG. 3A is a schematic perspective view illustrating the probe unit 10, and FIG. 3B is a schematic top view illustrating the probe unit 10. The probe unit 10 has a probe 11 which receives acoustic waves from a subject through the fixing member 22. The term "probe" herein refers to a transducer which receives acoustic waves and then converts the acoustic waves into electric signals. Any transducer which receives acoustic waves and then converts the acoustic waves into electric signals can be used, such as piezoelectric transducers utilizing a piezoelectric phenomenon, transducers utilizing optical resonance, and transducers utilizing a change in capacitance. Multiple transducers may be arrayed, or a single transducer may be provided.

The probe 11 is accommodated in a housing 12 and fixed thereto. The housing 12 has a sealing member 13 being a matching liquid-holding member and provided so as to surround the probe 11. A packing formed from rubber, a porous material (e.g., sponge), leather, or resin can be used as the sealing member 13. The housing 12 is pressed against the fixing member 22 with the sealing member 13 interposed therebetween, so that a space 15 can be formed between the fixing member 22 and the probe 11 to hold matching oil being a matching liquid for acoustic impedance matching. The matching oil is held in the space 15 defined by the fixing member 22, the probe 11, and the sealing member 13.

The upper side of the space 15 is opened to release air contained in the matching oil. In other words, an opening is provided to the upper side of the space 15. The subject-holding member-side surface of the housing 12 has a supply port 14 formed to supply the matching oil to the space 15. The matching oil is supplied from a tank (not illustrated) by using a pump (not illustrated). The pump is controlled by a micro controller or a computer (not illustrated). The matching liquid is preferably degased, and water or any other liquid than oil can be used. The tank holds the matching oil in an amount enough to fill the space between the fixing member 22 and the probe 11 from the beginning of an examination to the end.

An oil fence 12a is provided at the rear edge of the upper surface of the housing 12 (on the side of a cable 11a of the probe 11) and functions as a partition which prevents the matching oil on the housing 12 from flowing to the cable 11a. The partition of the present invention is preferably bent or formed from an elastic material so as to be deformable in response to application of stress. Since the partition is deformable, the probe unit 10 can be moved in close proximity to the counter member (supporting member 201 or another component) even in the case where the partition contacts the counter member.

The housing 12 has grooves 12b (side guide portion) and a guide sheet 17 (front guide portion) each constituting a guide for the matching oil. The guide sheet 17 is preferably deformable in response to application of stress from the fixing member 22 and is formed so as to allow the movement of the probe unit 10 even in a state in which the guide sheet 17 contacts the fixing member 22. A polyethylene terephthalate (PET) film can be used for the guide sheet 17.

The sizes, materials, shapes, and relative arrangement of the below-mentioned components of the guide should be appropriately changed depending on a variety of configurations and requirements of apparatuses to which the present invention is applied. The present invention should not be limited to the configuration described below.

Figure 4A:
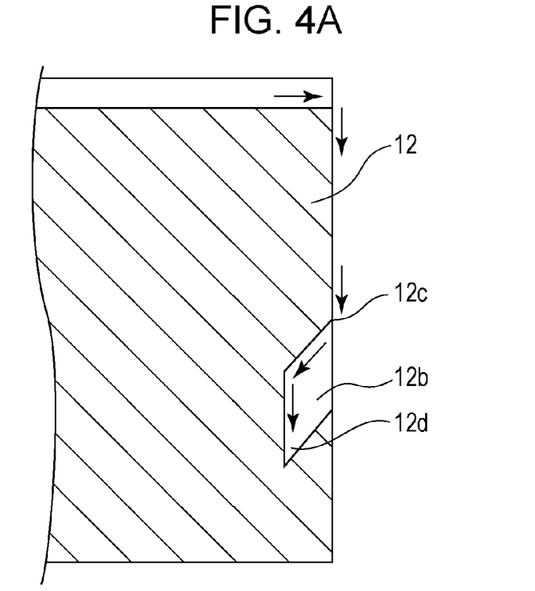
FIG. 4A is a schematic cross-sectional view illustrating a groove of a housing according to the first embodiment of the present invention.

Each groove 12b of the guide of the present embodiment is configured so as to extend toward the lower part of the housing 12 as approaching the fixing member 22 from the side of the oil fence 12a. FIG. 4A illustrates the cross-sectional structure with the groove 12b viewed in the direction indicated by an arrow IVA in FIG. 3A. Arrows in FIG. 4A schematically indicate the flow of the matching oil from the upper surface of the housing 12. The matching oil runs down the side surface of the housing 12 and then reaches the groove 12b. The groove 12b has an upper edge 12c with an obtuse angle, so that the matching oil can run along the shape of the groove 12b and then reaches a bottom 12d of the groove 12b. The angle of the edge 12c and the cross-sectional structure of the groove 12b are not limited to those of the present embodiment, and any structure can be employed provided that the matching oil running down the side surface can be caught and guided to the subject-holding member without being spilled from the groove 12b to the side surface of the housing 12.

Figure 4B:
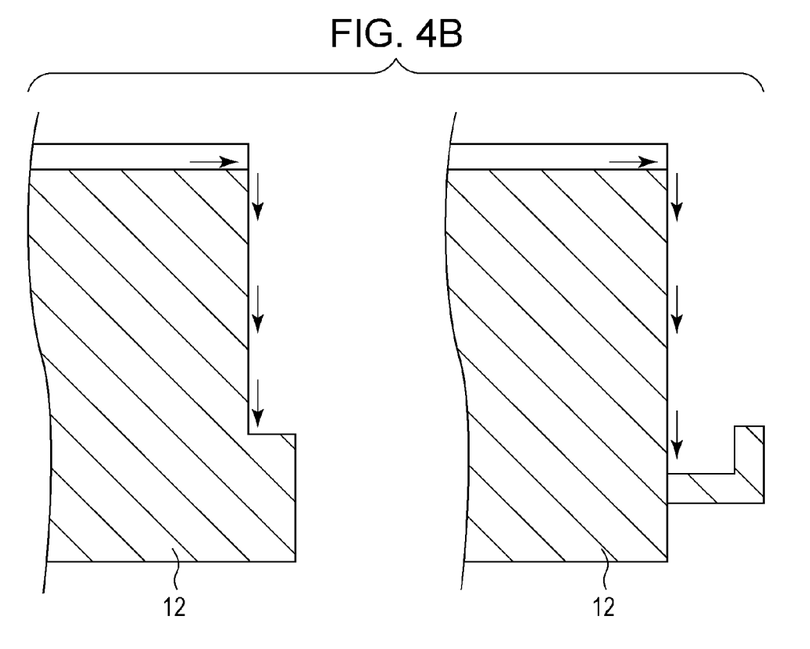
FIG. 4B is a schematic cross-sectional view illustrating modifications of the groove of the housing.

FIG. 4B illustrates modifications of the side guide portion. As illustrated in FIG. 4B, the side surface may have a step and a protrusion in place of the groove.

Figure 5A:
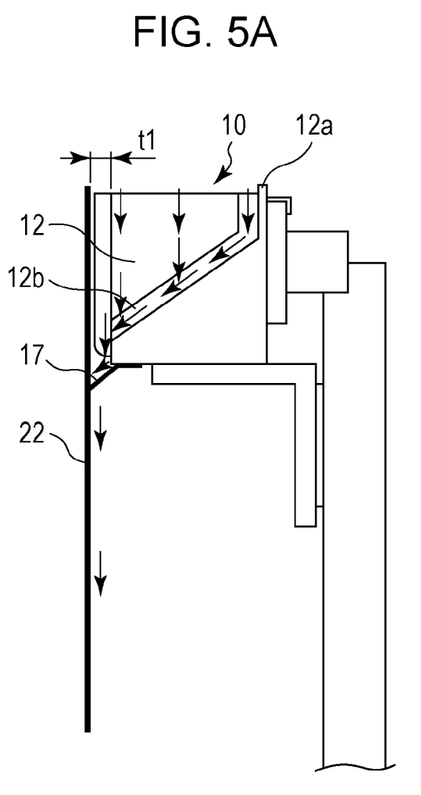
FIGS. 5A and 5B are schematic side views each illustrating a change in a state of a guide sheet according to an embodiment of the present invention.
Figure 5B:
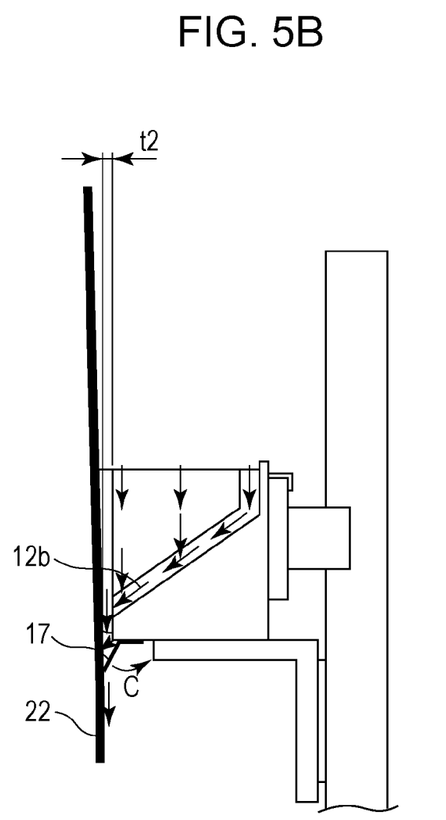

FIG. 5A is a side view illustrating the probe unit 10 and the fixing member 22 in a state in which a subject is not held, and FIG. 5B is a side view illustrating the probe unit 10 and the fixing member 22 in a state in which the fixing member 22 is bent as a result of holding a subject. The guide sheet 17 of the guide is bent obliquely downward from the housing 12. In particular, the level of the guide sheet 17 becomes decreased as the guide sheet 17 extends from the housing 12 to the fixing member 22. The matching oil to be guided by the guide sheet 17 thus flows on the upper surface of the guide sheet 17 and then is introduced to the fixing member 22. Even in the case where the fixing member 22 is deformed toward the probe unit 10 by pressing a subject for holding when the probe unit 10 is moved, force acts in a direction in which the guide sheet 17 is bent. In particular, the guide sheet 17 is deformable. Examples of a material of the guide sheet 17 include a sheet of PET, a sheet of another resin such as polycarbonate (PC), a plate having a spring property, and rubber.

The guide sheet 17 is bonded to the housing 12 with an adhesive exhibiting high sealing properties to prevent the leakage of the matching oil from the bonded portion. The guide sheet 17 and the housing 12 may be connected such that rubber or a porous material (e.g., sponge) is provided therebetween while being fixed with another component. The guide sheet 17 preferably has a width larger than a width A of the housing 12. The fixing member 22-side tip of the guide sheet 17 may not necessarily contact the fixing member 22 provided that the matching oil flowing on the upper surface of the guide sheet 17 can be introduced to the fixing member 22. A distance which enables the matching oil to be introduced to the fixing member 22 even though the guide sheet 17 does not contact the fixing member 22 can be determined depending on the physical properties of the matching oil to be used, such as surface tension and viscosity. If highly viscous matching oil flowing through each groove 12b directly contacts the fixing member 22 and then runs down the fixing member 22, the guide sheet 17 may not be provided. In other words, the guide of the present invention may have only the side guide portion without the front guide portion.

The space 15 defined by the fixing member 22, the probe 11, and the sealing member 13 (at least between the fixing member 22 and the probe 11) is filled with the matching oil during an examination. The subject-holding member-side surface of the housing 12 has a liquid surface sensor 16 provided at a level higher than that of the sensor 11. In the case where the liquid surface sensor 16 can detect the matching oil, it is determined that the space between the fixing member 22 and the probe 11 is filled with the matching oil.

In preparation for an examination, a result of detection by the liquid surface sensor 16 is viewed to determine whether the space 15 is filled with the matching oil or not. If a result of detection shows that the space 15 is filled with matching oil, preparation for the examination has been finished. Even in the case where the matching oil is spilled or leaked by the movement of the probe unit 10 during an examination, the matching oil is constantly supplied to the space 15 to maintain the amount enough for the examination.

Moving Route of Probe Unit

Figure 6:
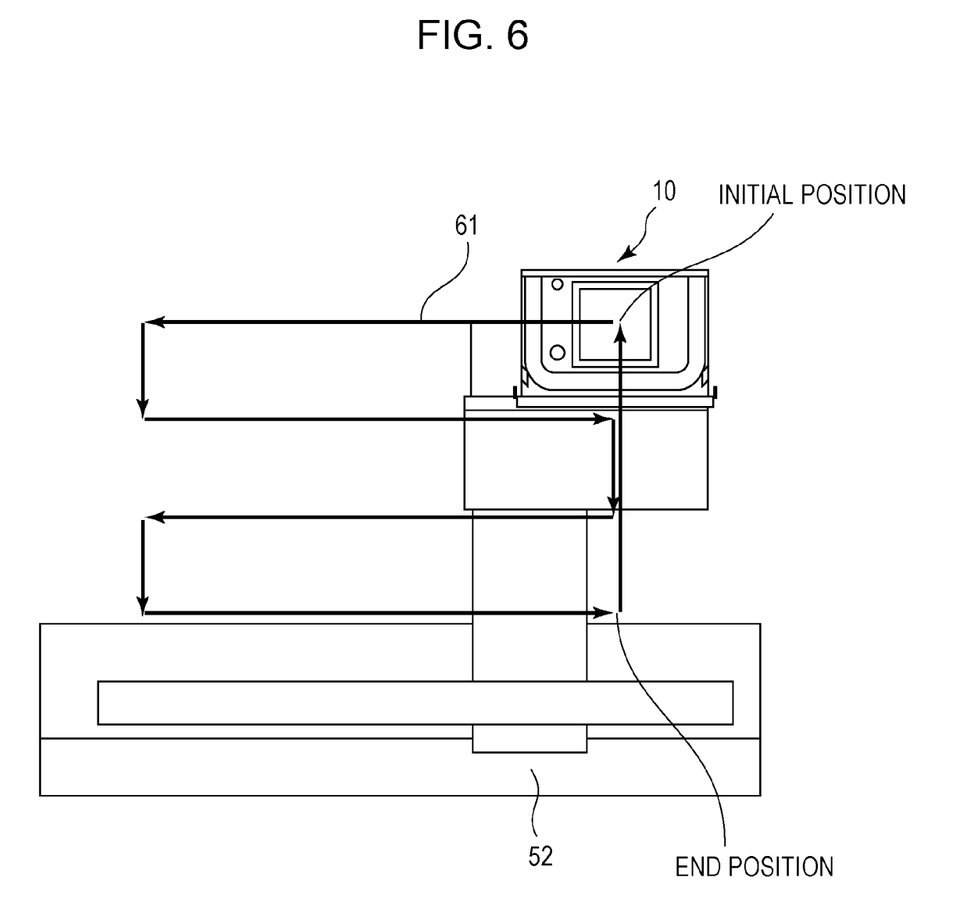
FIG. 6 is a schematic view illustrating a moving route of a probe unit according to an embodiment of the present invention.

A moving route of the probe unit 10 will now be described. FIG. 6 is a schematic view illustrating a moving route of the probe unit 10 during an examination. Arrows 61 indicate a route of the movement of the probe unit 10 during an examination.

The probe unit 10 is positioned at the uppermost position in an examination region (scanning region) at the initial stage of an examination. Once the examination has started, the probe unit 10 sequentially scans a subject in a horizontal direction in one scan line as indicated by the arrow 61 while receiving acoustic waves; then, the probe unit 10 moves below to the next scan line and scans the subject in the opposite direction in this scan line. These processes are repeated to scan the subject in every single line in sequence from the top. The probe unit 10 finally reaches the end position and then returns to the initial position to complete the examination. The scan procedure is not limited to such a procedure; the probe unit 10 may move from a lower position to an upper position to scan a subject, or a step-and-repeat process in which the probe unit 10 stops at receiving positions to receive acoustic waves may be employed. Traditional techniques can be used to create image data of information on a subject from electric signals output from the probe 11 which has received acoustic waves.

Flow of Matching Liquid

The flow of matching oil from the upper surface of the housing 12 will now be described. Arrows in FIGS. 5A and 5B schematically indicate the flow of the matching oil. In the case where the matching oil is leaked or spilled onto the upper surface of the housing 12, the matching oil runs down side surfaces of the housing 12 because the fixing member 22 and the oil fence 12a are provided in front of and in the rear of the housing 12, respectively. The matching oil runs down the side surfaces of the housing 12 to the grooves 12b and then is introduced to the front side (side of the fixing member 22) of the housing 12 along the grooves 12b. After the matching oil has reached the front side of the housing 12, the matching oil flows down to the guide sheet 17 along the housing 12.

Then, the matching oil flows down from two ends 17a of the guide sheet 17 (see, FIG. 3B) or the space between the fixing member 22 and the guide sheet 17 along the fixing member 22. In the case where a subject is held, the fixing member 22 is deformed by being bent, and the distance between the fixing member 22 and the housing 12 is therefore changed. For instance, a distance t1 is secured in FIG. 5A in which a subject is not held; on the other hand, the distance t1 is decreased to a distance t2 in FIG. 5B in which a subject is held.

The distance between the fixing member 22 and the housing 12 also changes depending on the position of the probe unit 10. As described above, the guide sheet 17 can be deformed in response to application of stress from the fixing member 22. In the case where the distance between the fixing member 22 and the housing 12 is decreased, the tip of the guide sheet 17 shifts in the direction indicated by an arrow C. In the case where the distance therebetween is increased, the guide sheet 17 starts to return to the initial shape; thus, the tip of the guide sheet 17 shifts toward the fixing member 22. Hence, even though the distance between the fixing member 22 and the housing 12 is changed, the matching oil can be always guided from the guide sheet 17 to the fixing member 22. Consequently, even in the case where the fixing member 22 is deformed as a result of holding a subject, the matching oil can be guided to the fixing member 22.

Although the guide sheet 17 of the present embodiment is a single component, the present invention should not be limited to such a structure. The guide sheet 17 preferably has a structure which can be deformed in synchronism with the deformation of the fixing member 22; for example, a base may be formed from a rigid material such as aluminum, and a rubber sheet may be used to form only a portion which contacts the fixing member 22. Furthermore, a spring may be used to urge the guide sheet 17 against the fixing member 22.

In the configuration of the present embodiment, the matching oil which has spilled onto the upper surface of the housing 12 can be introduced to the fixing member 22 by the guide which includes grooves (steps or protrusions) as the side guide portion provided to the side surfaces of the housing 12 and the guide sheet as the front guide portion. The guide sheet 17 can be deformed in response to application of stress; thus, even in the case where the probe unit 10 is moved in a state in which the fixing member 22 is deformed as a result of holding a subject, the matching oil can be guided to the fixing member 22.

Second Embodiment

Figure 7A:
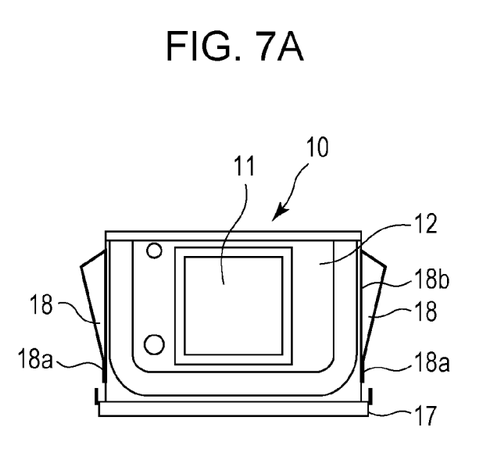
FIG. 7A is a schematic front view illustrating a probe unit according to a second embodiment of the present invention.
Figure 7B:
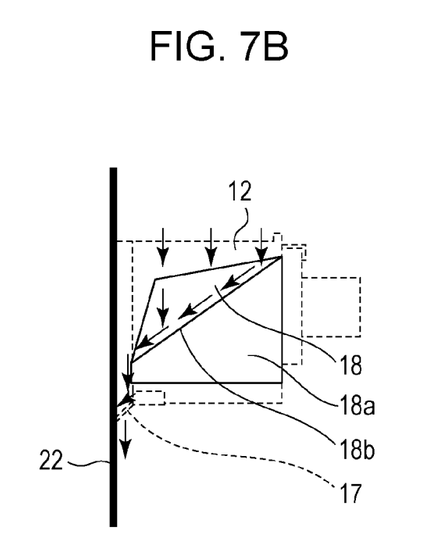
FIG. 7B is a schematic side view illustrating the probe unit according to the second embodiment of the present invention.

The present embodiment is different from the first embodiment in the configuration of the guide. FIG. 7A is a schematic front view illustrating the probe unit 10 of a second embodiment, and FIG. 7B is a schematic side view illustrating the probe unit 10 of the second embodiment. In the second embodiment, side guide sheets 18 are provided as the side guide portion on the side surfaces of the housing 12 in place of the grooves. Each side guide sheet 18 is formed from, for example, a PET film. Each side guide sheet 18 has a bonded part 18a attached to the housing 12 and a folded part 18b at which the side guide sheet 18 is folded in an oblique direction. Each side guide sheet 18 is bonded to the housing 12 at the bonded part 18a with an adhesive exhibiting sealing properties to prevent the leakage of the matching oil therefrom. The housing 12 and each side guide sheet 18 may be connected such that rubber or a porous material (e.g., sponge) is provided therebetween while being fixed with another component.

Arrows in FIG. 7B schematically indicate the flow of the matching oil. The matching oil which has run down the side surfaces of the housing 12 to the side guide sheets 18 is introduced to the front side of the housing 12 (side of the fixing member 22) along the folded portions 18b of the side guide sheets 18. The matching oil which has reached the front side of the housing 12 falls down to the guide sheet 17 along the housing 12. The guide sheet 17 of the present embodiment functions as the front guide portion as in the first embodiment.

The amount of the flowing matching oil increases in some cases depending on the driving speed of the probe unit 10. In the case where the probe unit 10 is driven at a high speed (fast), for example, the amount of the matching oil to be spilled increases; thus, the amount of the flowing matching oil becomes increased in some cases. In the first embodiment, an increase in the amount of the matching oil flowing from the housing 12 onto its side surface causes the side guide portions, such as grooves or protrusions, to have increased size adequate for the increased amount of the flowing matching oil. In such a case, formation of the side guide portion may fall into difficulty, or the size of the housing 12 may be increased in proportion to an increase in the size of the grooves. Hence, the side guide portion of the present embodiment has a configuration effective to the matching oil flowing in a large amount.

In the present embodiment, each side guide sheet 18 being the side guide portion and the guide sheet 17 being the front guide portion are separately provided; however, these components may be integrally provided. In particular, each side guide sheet 18 may be extended across the front surface (probe 11—side surface) of the housing 12 to the side of the fixing member 22 and function also as the front guide portion. The guide having such a configuration can also introduce the matching oil to the fixing member 22.

Even in the case where each side guide sheet 18 has the configuration illustrated in FIGS. 7A and 7B, the guide sheet 17 may not be formed, provided that highly viscous matching oil running down each side guide sheet 18 can directly contact the fixing member 22 and then run down the fixing member 22. In other words, only the side guide portion can serve as the guide of the present invention without use of the front guide portion.

As described above, in the present embodiment, each side guide sheet 18 provided to the housing 12 as the side guide portion can also introduce the matching oil flowing from the upper surface of the housing 12 to the fixing member 22.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-043808 filed Feb. 29, 2012, which is hereby incorporated by reference herein in its entirety.

What is claimed is:

1. A subject information acquiring apparatus comprising:
a subject-holding member configured to hold a subject; and
a probe unit having a transducer which receives acoustic waves from the subject through the subject-holding member, a housing which accommodates the transducer, and a matching liquid-holding member configured to hold a matching liquid between the transducer and the subject-holding member, the probe unit being allowed to move relative to the subject-holding member, wherein
the probe unit has a guide which directs the matching liquid to the subject-holding member, wherein the matching liquid, having been spilled onto an upper surface of the housing from a space defined by the matching liquid-holding member, the transducer, and the subject-holding member, is then flowed from the upper surface of the housing to an area of the subject-holding member other than the area of the subject-holding member that defines said space; and
wherein a side surface of the housing that faces the subject-holding member has a supply port and a sensor, the supply port being configured to supply the matching liquid to the space, and the sensor detecting the matching liquid.

2. The subject information acquiring apparatus according to claim 1, wherein the guide is provided to the housing and introduces the matching liquid flowing from the upper surface of the housing to the subject-holding member.

3. The subject information acquiring apparatus according to claim 2, wherein at least part of the guide is a groove formed in the housing.

4. The subject information acquiring apparatus according to claim 1, wherein the guide includes a side guide portion and a front guide portion, the side guide portion being provided to the housing to introduce a matching liquid to the subject-holding member side of the housing, and the front guide portion introducing the matching liquid introduced by the side guide portion to the subject-holding member.

5. The subject information acquiring apparatus according to claim 1, wherein at least part of the guide is deformed depending on the shape of the subject-holding member being in a state in which a subject is held.

6. The subject information acquiring apparatus according to claim 1, wherein the probe unit has a partition which blocks the flow of the matching liquid past a rear area of the housing.

* * * * *